[12] United States Patent
Bonaldo et al.

(10) Patent No.: US 8,487,008 B2
(45) Date of Patent: Jul. 16, 2013

(54) TREATMENT OF MUSCULAR DYSTROPHIES AND ASSOCIATED CONDITIONS BY ADMINISTRATION OF MONOAMINE OXIDASE INHIBITORS

(75) Inventors: Paolo Bonaldo, Padua (IT); Marcella Canton, Padua (IT); Fabio DiLisa, Padua (IT); Sara Menazza, Padua (IT)

(73) Assignee: Universita degli Studi di Padova, Pado (IT)

( * ) Notice: Subject to any disclaimer, the term of this patent is extended or adjusted under 35 U.S.C. 154(b) by 0 days.

(21) Appl. No.: 13/166,688

(22) Filed: Jun. 22, 2011

(65) Prior Publication Data

US 2012/0329800 A1 Dec. 27, 2012

(51) Int. Cl.
*A61K 31/135* (2006.01)
(52) U.S. Cl.
USPC ........................................................ 514/651
(58) Field of Classification Search
USPC ........................................................ 514/651
See application file for complete search history.

(56) References Cited

U.S. PATENT DOCUMENTS 4,683,195 A 7/1987 Mullis et al.
2009/0286883 A1 11/2009 Dilisa et al.

OTHER PUBLICATIONS

Magyar et al. CAS: 87: 147793, 1997.*
Ali et al. CAS: 116: 50904, 1992.*
O'Brien et al. CAS: 123: 25165, 1995.*
Menazza et al. CAS: 154:7287, 2010.*
Angelin A, et al., "Mitochondrial dysfunction in the pathogenesis of Ullrich congenital muscular dystrophy and prospective therapy with cyclosporins." Proc Natl Acad Sci U S A. 2007;104(3):991-6.
Benov L, et al., "Critical evaluation of the use of hydroethidine as a measure of superoxide anion radical." Free Radic Biol Med. 1998;25(7):826-31.
Bianchi et al. "A new hypertrophic mechanism of serotonin in cardiac myocytes: receptor-independent ROS generation." FASEB J. 2005;19(6):641-3.
Bianchi et al. "Oxidative stress by monoamine oxidase mediates receptor-independent cardiomyocyte apoptosis by serotonin and postischemic myocardial injury." Circulation. 2005;112(21):3297-3305.
Billett. Monoamine oxidase (MAO) in human peripheral tissues. Neurotoxicology. 2004;25(1-2):139-148.
Blaauw B, et al., "Akt activation prevents the force drop induced by eccentric contractions in dystrophin-deficient skeletal muscle." Hum Mol Genet. 2008;17(23):3686-96.
Blaauw B, et al., "Eccentric contractions lead to myofibrillar dysfunction in muscular dystrophy." J Appl Physiol. 2010;108(1):105-11.
Bonaldo P, et al., "Collagen VI deficiency induces early onset myopathy in the mouse: an animal model for Bethlem myopathy." Hum Mol Genet. 1998;7(13):2135-40.
Brunner et al. "Abnormal behavior associated with a point mutation in the structural gene for monoamine oxidase A." Science. 1993;262(5133):578-580.
Canton M, et al., "Oxidative modification of tropomyosin and myocardial dysfunction following coronary microembolization." Eur Heart J. 2006;27(7):875-81.
Coatrieux et al. "MAO-A-induced mitogenic signaling is mediated by reactive oxygen species, MMP-2, and the sphingolipid pathway." Free Radical Biology & Medicine. 2007;43:80-89.
Di Lisa et al. "Mitochondria and cardioprotection." Heart Fil Rev. 2007;12:249-260.
Di Lisa et al. "Mitochondria and vascular pathology." Pharmacological Reports. 2009;61:123-130.
Di Lisa et al. "Mitochondria pathways for ROS formation and myocardial injury: the relevance of p66Shc and monoamine oxidase." Basic Res Cardiol. 2009;104:131-139.
Disatnik MH, et al., "Evidence of oxidative stress in mdx mouse muscle: studies of the pre-necrotic state." Neurol Sci. 1998;161(1):77-84.
Durbeej M, and Campbell KP. "Muscular dystrophies involving the dystrophin-glycoprotein complex: an overview of current mouse models." Curr Opin Genet Dev. 2002;12(3):349-61.
Halliwell. "Reactive oxygen species and the central nervous system." J Neurochem. 1992;59(5):1609-1623.
Irwin WA, et al., "Mitochondrial dysfunction and apoptosis in myopathic mice with collagen VI deficiency." Nat Genet. 2003;35(4):367-71.
Kaludercic et al. "Monoamine Oxidase A-Mediated Enhanced Catabolism of Norepinephrine Contributes to Adverse Remodeling and Pump Failure in Hearts iwth Pressure Overload." Circ. Res. 2010;106:193-202.
Kumar et al. "Oxidative alpha-ketoglutarate dehydrogenase inhibition via subtle elevations in monoamine oxidase B levels results in loss of spare respiratory capacity: implications for Parkinson's disease." J Biol Chem. 2003;278(47):46432-46439.
Lairez et al. "Genetic deletion of MAO-A promotes serotonin-dependent ventricular hypertrophy by pressure overload." Journal of Molecular and Cellular Cardiology. 2009;46:587-595.
Lamensdorf et al. "Metabolic stress in PC12 cells induces the formation of the endogenous dopaminergic neurotoxin, 3,4-dihydroxyphenylacetaldehyde." J Neurosci Res. 2000;60(4):552-558.
Lenders et al. "Specific genetic deficiencies of the A and B isoenzymes of monoamine oxidase are characterized by distinct neurochemical and clinical phenotypes." J Clin Invest. 1996;97(4):1010-1019.
Menazza et al., "Oxidative stress by monamine oxidases is causally involved in myofiber damage in muscular dystrophy." Hum. Mol. Gen., 2010, vol. 19, No. 21 pp. 4207-4215.
Merlini L, et al., "Cyclosporin A corrects mitochondrial dysfunction and muscle apoptosis in patients with collagen VI myopathies." Proc Natl Aced Sci U S A. Apr. 1, 2008;105(13):5225-9.
Partanen et al. "Histochemically demonstrable monoamine oxidase activity in the adult human heart in various cardiac diseases." Virchows Arch A Pathol Anat Histol. 1976;370(4):291-296.
Pchejetski et al. "Oxidative Stress-Dependent Sphingosine Kinase-1 Inhibition Mediates Monoamine Oxidase A-Associated Cardiac Cell Apoptosis." Circ. Res. 2007;100:41-49.

(Continued)

*Primary Examiner* — Rei-tsang Shiao
(74) *Attorney, Agent, or Firm* — Foley & Lardner LLP

(57) ABSTRACT

Administration of a monoamine oxidase inhibitor is useful in the prevention and treatment of muscle dystrophy. Methods and compositions for inhibiting the production of reactive oxygen species in a muscle cell overproducing reactive oxygen species are provided herein.

8 Claims, 7 Drawing Sheets

OTHER PUBLICATIONS

Petronilli V, et al., "Transient and long-lasting openings of the mitochondrial permeability transition pore can be monitored directly in intact cells by changes in mitochondrial calcein fluorescence." Biophys J. Feb. 1999;76(2):725-34.

Qin et al., "Selegiline attenuates cardiac oxidative stress and apoptosis in heart failure: association with improvement of cardiac function," 2003, European Journal of Pharmacology, vol. 461, pp. 149-158.

Rossi R, et al., "Response to caffeine and ryanodine receptor isoforms in mouse skeletal muscles." Am J Physiol Cell Physiol. Aug. 2001;281(2):C585-94.

Shih et al. "Regulation of MAO-A and MAO-B gene expression." Curr Med Chem. 2004;11(15):1995-2005.

Shih. "Cloning, after cloning, knock-out mice, and physiological functions of MAO-A and B." Neurotoxicology. 2004;25(1-2):21-30.

Tidball JG, Wehling-Henricks M. "The role of free radicals in the pathophysiology of muscular dystrophy." J Appl Physiol. Apr. 2007;102(4):1677-86.

Villeneuve et al. "Dose-dependent activation of distinct hypertrophic pathways by serotonin in cardiac cells." Am J Physiol Heart Circ Physiol. 2009;297:H821-H828.

Yang et al. Calcineurin-mediated BAD Ser155 dephosphorylation in ammonia-induced apoptosis of cultured rat hippocampal neurons. Neurosci Lett. 2004;357(1):73-75.

Youdim et al. "Therapeutic applications of selective and non-selective inhibitors of monoamine oxidase A and B that do not cause significant tyramine potentiation." Neurotoxicology. 2004;25(1-2):243-250.

Youdim et al. "New directions in monoamine oxidase A and B selective inhibitors and substrates." Biochem Pharmacol. 1991;41(2):155-162.

Youdim et al. "The therapeutic potential of monoamine oxidase inhibitors." Nat Rev Neurosci. 2006;7(4):295-309.

* cited by examiner

TREATMENT OF MUSCULAR DYSTROPHIES AND ASSOCIATED CONDITIONS BY ADMINISTRATION OF MONOAMINE OXIDASE INHIBITORS

FIELD OF THE INVENTION

The present invention relates generally to the field of medicine, pharmaceutical chemistry, biology and in particular to methods for treating muscle dystrophies and muscle degeneration.

BACKGROUND OF THE INVENTION

Muscle dystrophies (MDs) are a heterogeneous group of inherited human disorders primarily affecting skeletal muscles. Typically, MDs show diffuse wasting and weakness of muscles, associated with degeneration and regeneration of muscle fibers. Duchenne MD is the most common and severe form of MD worldwide. This progressive and lethal X-linked myopathy is characterized by a deficiency of dystrophin, a subsarcolemmal protein critical in membrane stabilization and prevention of contraction-induced cell membrane damage (Durbeej, M. and Campbell, K. P. (2002) Curr. Opin. Genet. Dev., 12, 349-361).

There is no known cure for muscular dystrophy (MD). Inactivity (such as bed rest and even sitting for long periods) can worsen the disease. Physical therapy, occupational therapy, orthotic intervention (e.g., ankle-foot orthosis), speech therapy and orthopedic instruments (e.g., wheelchairs and standing frames) may be helpful.

There is no specific treatment for any of the forms of MD. Physical therapy to prevent contractures and maintain muscle tone, orthoses (orthopedic appliances used for support) and corrective orthopedic surgery may be needed to improve the quality of life in some cases. Thus, there is a need in the art for improved methods of treatment for MDs.

SUMMARY OF THE INVENTION

This invention is directed towards methods for preventing and treating conditions associated with a group of genetic diseases referred to as muscular dystrophies. In one aspect, the invention provides method of inhibiting the production of reactive oxygen species in a muscle cell overproducing reactive oxygen species which method comprises contacting the cell with an effective amount of a monoamine oxidase inhibitor compound of Formula I:

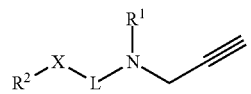

I wherein $R^1$ is H or $C_1$-$C_6$ alkyl;

L is a covalent bond or $C_1$-$C_6$ straight chain or branched alkylene;

X is a covalent bond or O, S, or N;

$R^2$ is an aryl, heteroaryl, heterocycle, cycloalkyl, cycloalkenyl, each of which can optionally be substituted with 1-3 substituents selected from halogen or nitrogen; and wherein the muscle cell is not a cardiomyocyte.

In another aspect, the invention provides a method for preventing or treating MD wherein the etiology of said MD includes overproducing reactive oxygen species which method comprises administering a therapeutically effective amount of a compound of formula I to reduce or prevent the production of reactive oxygen species, thereby treating and/or improving MD.

In another aspect, the invention provides a compound of Formula I provided that the compound is not a compound tabulated in Table 1 below:

TABLE 1

| Structure | Common Name | IUPAC name |
|---|---|---|
| 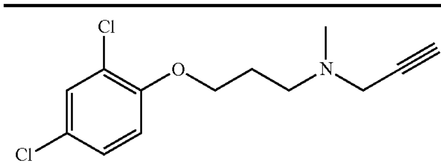 | Clorgiline | N-[3-(2,4-dichlorophenoxy)propyl]-N-methyl-prop-2-yn-1-amine |
| 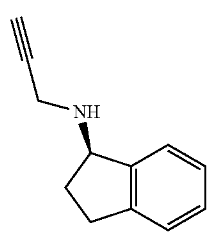 | Rasagiline | (R)-N-(prop-2-ynyl)-2,3-dihydro-1H-inden-1-amine |
| 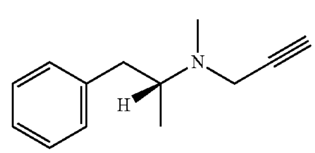 | Selegline | (R)-N-methyl-N-(1-phenylpropan-2-yl)prop-2-yn-1-amine |
| 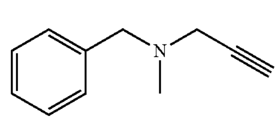 | Pargyline | N-Benzyl-N-methylprop-2-yn-1-amine |

BRIEF DESCRIPTION OF THE FIGURES

FIG. 1A: MAO activity in gastrocnemius muscles from wild-type and Col6a1$^{-/-}$ mice after 1 week of treatment with pargyline or vehicle. FIG. 1B: Representative western blots (WB) of MAO-A and MAO-B in diaphragm and gastrocnemius from wild-type (n=6) and Col6a1$^{-/-}$ (n=6) mice. Equal protein loading was indicated by Red Ponceau staining FIG. 1C: Oxidative stress assessed by DHE staining in sections of diaphragm from vehicle- or pargyline-treated wild-type and Col6a1$^{-/-}$ mice. Scale bar, 50 µm. FIG. 1D: Quantification of DHE fluorescence in gastrocnemius, diaphragm and tibialis anterior (TA) muscle cryosections from wild-type and Col6a1$^{-/-}$ mice treated with vehicle or pargyline showing the reduced ROS accumulation after pargyline treatment. Parg, pargyline; veh, vehicle; WT, wild-type. *P<0.05 Col6a1$^{-/-}$-veh versus WT-veh; #P<0.05 Col6a1$^{-/-}$-veh versus Col6a1$^{-/-}$-parg. Error bars represent the s.e.m. The number of mice for each group is indicated inside each bar.

FIG. 2A: Tm oxidation detected as the formation of DCB in diaphragm muscles of vehicle- or pargyline-treated wild-type and Col6a1$^{-/-}$ mice. High-molecular-mass peptides were attributed to DCB formation by comparing electrophoreses carried out in the absence or in the presence of β-mercaptoethanol (β-me). Immunoblotting displayed additional high-molecular-mass bands in Col6a1$^{-/-}$ diaphragm that were reduced by pargyline treatment. FIG. 2B: Quantitative analysis of DCB formation in Tm immunoblots showing a significant decrease in Tm oxidation upon pargyline treatment. Parg, pargyline; veh, vehicle; WT, wild-type. #P<0.05 Col6a1$^{-/-}$-veh versus WT-veh; #P<0.05 Col6a1$^{-/-}$-veh versus Col6a1$^{-/-}$-parg. Error bars represent the s.e.m. The number of mice for each group is indicated inside each bar.

FIG. 3A: Quantification of apoptotic nuclei by TUNEL assay in diaphragm sections. Pargyline treatment prevented the increased incidence of apoptosis in Col6a1$^{-/-}$ mice. FIG. 3B: Quantification of the necrotic fibers by means of the immunohistochemical staining for IgG in diaphragm sections. IgG-positive fibers were present in Col6a1$^{-/-}$ mice and their number was decreased by pargyline treatment. FIG. 3C: Representative images of diaphragms from wild-type and Col6a1$^{-/-}$ mice, following vital staining with Evans blue dye. Diaphragms were isolated from wild-type (n=5) and Col6a1$^{-/-}$ (n=5) mice treated with vehicle or pargyline and examined by light microscopy. Diaphragms from Col6a1$^{-/-}$ mice displayed a marked incidence of damaged fibers, identified by deep blue striations, which was reduced after pargyline treatment. FIG. 3D: Representative cross-sections of H&E staining from tibialis anterior muscle from wild-type and Col6a1$^{-/-}$ mice treated with vehicle or pargyline. Col6a1$^{-/-}$ muscles showed a large variability in myofiber size while pargyline-treated Col6a1$^{-/-}$ mice displayed uniform myofiber size, similar to wild-type muscles. Scale bar, 100 µm. FIG. 3E: Analysis of fiber CSAs in diaphragm and tibialis anterior (TA) muscle of pargyline- or vehicle-treated wild-type and Col6a1$^{-/-}$ mice. Parg, pargyline; veh, vehicle; WT, wild-type. *P<0.05 Col6a1$^{-/-}$-veh versus WT-veh; #P<0.05 Col6a1$^{-/-}$-veh versus Col6a1$^{-/-}$-parg. Error bars represent the s.e.m. The number of mice for each group is indicated inside each bar. The key in FIG. 3A applies to all panels in FIG. 3.

FIG. 4A: Tension development by single-skinned fibers of gastrocnemius from vehicle-treated Col6a1$^{-/-}$, pargyline-treated Col6a1$^{-/-}$ and vehicle-treated wild-type mice. Col6a1$^{-/-}$ muscles developed lower isometric tension than wild-type fibers. The contractile impairment disappeared in the fibers of pargyline-treated Col6a1$^{-/-}$ mice. n=22 or more fibers for each group. FIG. 4B: Force-frequency curves of gastrocnemius muscle from vehicle-treated or pargyline-treated Col6a1$^{-/-}$ mice showed a significant increase in the normalized force of gastrocnemius muscle upon pargyline treatment. n=13 or more muscles for each group. P=0.0016 by a two-way analysis of variance. FIG. 4C: Locomotor performance measured on the running wheel as the average distance covered in 24 h. Pargyline-treated Col6a1$^{-/-}$ mice showed a significant recovery of the exercise performance. Parg, pargyline; veh, vehicle; WT, wild-type. *P<0.05 Col6a1$^{-/-}$-veh versus WT-veh; #P<0.05 Col6a1$^{-/-}$-veh versus Col6a1$^{-/-}$-parg. Error bars represent the s.e.m. The number of mice for each group is indicated inside each bar or between parentheses for FIG. 4B. The key in FIG. 4A applies to all panels.

FIG. 5A: DCB formation in Tm detected by immunoelectrophoresis of myofibrillar samples from gastrocnemius and quadriceps muscles, as detailed in FIG. 2A. Immunoblotting analyses showed that the additional high-molecular-mass bands in Col6a1$^{-/-}$ muscles were significantly reduced by pargyline treatment. FIG. 5B: Quantitative analysis of DCB formation in Tm immunoblots. Parg, pargyline; veh, vehicle; WT, wild-type, β-mercaptoethanol (β-me). *P<0.05 mdx-veh versus WT-veh; #P<0.05 mdx-veh versus mdx-parg. Error bars represent s.e.m. The number of mice for each group is indicated inside each bar.

FIG. 6A: Representative cross-sections of H&E-staining of gastrocnemius (Gastroc.) and quadriceps (Quadr.) muscles from wild-type and mdx mice treated with vehicle or with pargyline. Mdx muscles showed a large variability in myofiber size and occurrence of inflammatory infiltrates (arrows). On the contrary, mdx-treated mice displayed uniform fibers size and absence of inflammatory infiltrates, similarly to wild-type muscles. Scale bar, 100 µm. FIG. 6B: Morphometric analysis of myofiber CSAs in gastrocnemius muscles of wild-type and mdx mice treated with vehicle or pargyline. FIG. 6C: Quantification of apoptotic nuclei by TUNEL assay in diaphragm muscle sections. Pargyline treatment blunted the increased incidence of apoptosis in mdx mice. Parg, pargyline; veh, vehicle; WT, wild-type. *P<0.05 mdx-veh versus WT-veh; #P<0.05 mdx-veh versus mdx-parg. Error bars represent the s.e.m. The number of mice for each group is indicated inside each bar.

DETAILED DESCRIPTION OF THE INVENTION

Figure 1:
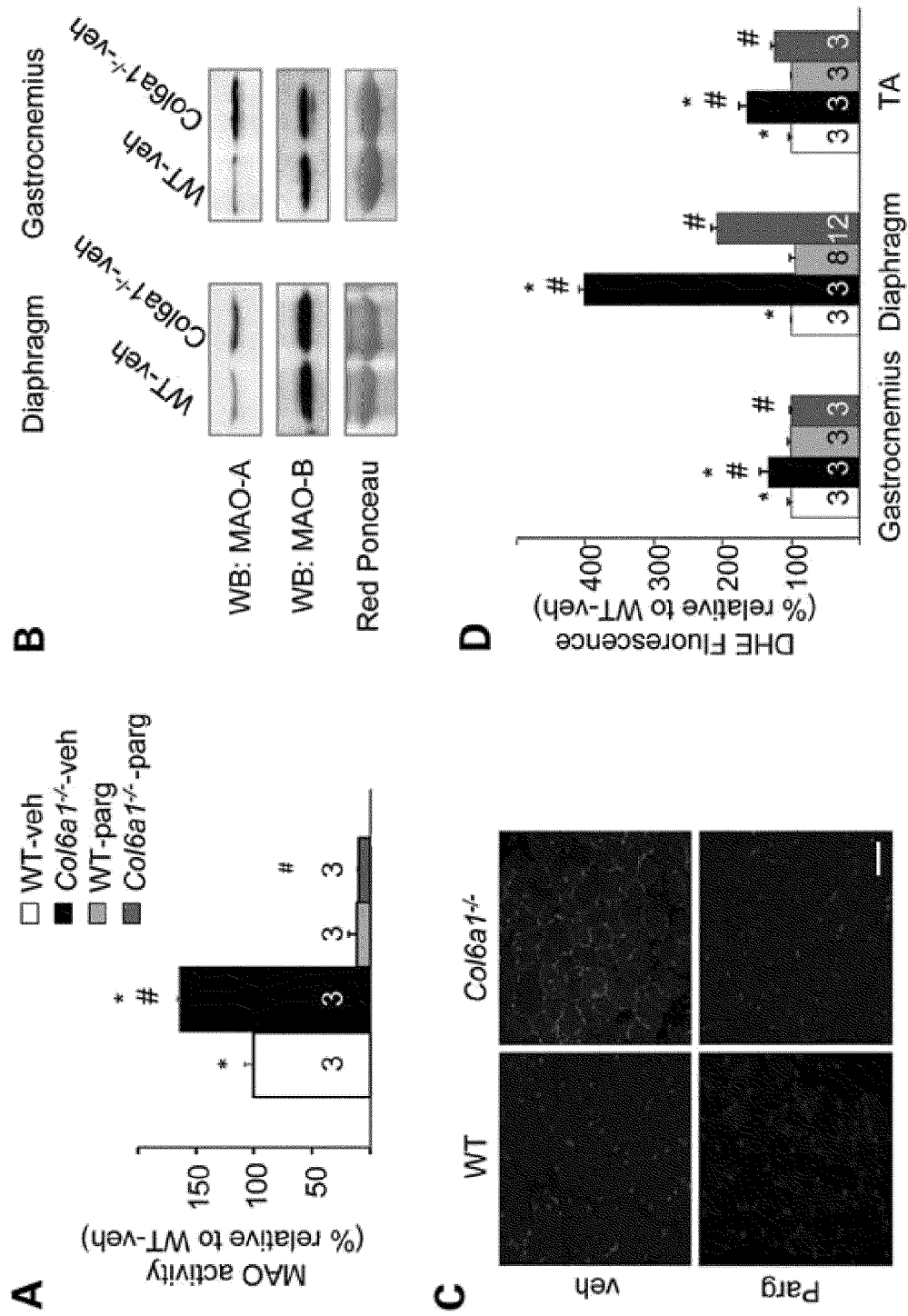
FIG. 1 shows that MAO inhibition reduces oxidative stress in Col6a1$^{-/-}$ mice.

Before the compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

The practice of the present invention will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, $3^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, $5^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Herzenberg et al. eds (1996) Weir's Handbook of Experimental Immunology; Manipulating the Mouse Embryo: A Laboratory Manual, $3^{rd}$ edition (Cold Spring Harbor Laboratory Press (2002)).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

1. DEFINITIONS

As used herein, certain terms may have the following defined meanings. As used in the specification and claims, the singular form "a," "an" and "the" include singular and plural references unless the context clearly dictates otherwise.

The term "comprising" is intended to mean that the compounds and methods include the recited elements, but not excluding others. "Consisting essentially of" when used to define compositions and methods, shall mean excluding other elements of any essential significance to the compounds or methods. "Consisting of" shall mean excluding more than trace elements of other ingredients for claimed compounds and substantial method steps. Embodiments defined by each of these transitional terms are within the scope of this invention. Accordingly, it is intended that the processes and compositions can include additional steps and components (comprising) or alternatively include additional steps and compounds of no significance (consisting essentially of) or alternatively, intending only the stated methods steps or compounds (consisting of).

As used herein, "mammals" include, but are not limited to, murines, rats, simians, humans, farm animals, sport animals and pets.

As used herein, "monoamine oxidases" or "monamine oxidase proteins" are enzymes that catalyze the oxidation of monoamines. Two monoamine oxidase (MAO) isoenzymes, MAO-A and MAO-B, are closely linked in opposite orientation on the X chromosome and are expressed in the outer mitochondrial membrane. In vivo, MAO-A and MAO-B oxidize monoamine neurotransmitters and dietary monoamines, the regulation of which is important in maintaining normal mental states. MAO-A prefers serotonin and norepinephrine substrates, whereas MAO-B prefers phenylethylamine, dopamine and trace amines. These proteins have been sequenced and characterized, see for example, the National Center for Biotechnology Information (NCBI) GenBank Accession Nos. for MAO-A gi|57284114|emb|CAI43120.1| [57284114]; gi|57209563|emb|CAI42421.1|[57209563]; gi|4557735|ref|NP_000231.1|[4557735]; gi|54402320|gb|AAV34720.1|[54402320]; gi|54402314|gb|AAV34717.1|[54402314]; gi|54402302|gb|AAV34711.1|[54402302]; gi|54402290|gb|AAV34705.1|[54402290]; gi|57284213|emb|CAI43216.1|[57284213] or gi|57209566|emb|CAI42424.1|[57209566] and the GenBank Accession Nos. for MAO-B gi|57209948|emb|CAI42522.1|[57209948]; gi|187376|gb|AAA59551.1|[187376]; gi|38202207|ref|NP_000889.3|[38202207]; gi|57209564|emb|CAI42422.1|[57209564]; gi|57208148|emb|CAD92552.2|[57208148]; gi|18490291|gb|AAH22494.1|[18490291]; gi|553527|gb|AAB46386.1|[553527] or gi|187359|gb|AAA59550.1|[187359].

As used herein, "monoamine oxidase inhibitor" or "MAO inhibitor" refers to a compound that acts by inhibiting the activity of monoamine oxidase, including MAO-A and/or MAO-B. In one aspect, MAO inhibitors prevent the breakdown of monoamine neurotransmitters thereby increasing their in vivo availability. In another aspect, MAO inhibitors prevent the catabolism of dietary monoamines. In yet another aspect, MAO inhibitors prevent generation of reactive oxygen species (ROS). MAO inhibitors are well known in the art and are used for the treatment of neurodegenerative diseases. Examples of MAO-A inhibitors include, but are not limited to, Clorgyline, Minaprine, and the reversible MAO-A inhibitors Befloxatone, Brofaromine, Cimoxatone, Harmaline, Moclobemide, Pirlindole and Toloxatone. Examples of MAO-B inhibitors include, but are not limited to, Rasagiline, Selegiline and Pargyline. Examples of unselective MAO-A and MAO-B inhibitors include, but are not limited to, Iproclozide (Sursum), Iproniazid (Marsilid, Iprozid, Ipronid, Rivivol, Propilniazida), Isocarboxazid (Marplan), Mebanazine (Actomol), Metfendrazine (H.M.-11), Nialamide (Niamid), Phenelzine (Nardil), Pheniprazine (Caton), Phenoxypropazine (Drazine), Pivalylbenzhydrazine (Tersavid, Neomarsilid), Safrazine (Safra) and Tranylcypromine (Parnate). See, for example, Remington: The Science and Practice of Pharmacy, 21st Edition, (2005, Lippincott Williams & Wilkins), pages 1517-1523, and Physicians' Desk Reference, Edition 60 (2006, Thomson PDR) page 1499 (each of which is incorporated herein by reference).

As used herein, "preventing" or "prevention" of a disease, disorder, symptom or condition means that the onset of the disease, disorder, symptom or condition in a mammal predisposed thereto is prevented such that the mammal does not manifest the disease, disorder, symptom or condition.

As used herein, "inhibit," "inhibiting," "reduce" or "reducing" or any variation of these terms includes any measurable decrease or complete inhibition to achieve a desired result.

As used herein, a "therapeutically effective amount" or an "effective amount" is used synonymously with and intends an amount sufficient to effect beneficial or desired results. An effective amount can be administered in one or more administrations, applications, or dosages.

As used herein, the term in vitro administration refers to manipulations performed on cells removed from or outside of a subject, including, but not limited to cells in culture.

The term in vivo administration includes all manipulations performed within a subject, including administrations.

As used herein, "treating" or "treatment" of a disease, disorder, symptom or condition will depend on the disease, disorder, symptom or condition to be treated, and the mammal to be treated. In general, treatment intends one or more of inhibiting the progression of the manifested disease, disorder, symptom or condition as measured by clinical or sub-clinical parameters (where the term "inhibiting" or "inhibition" is intended to be a subset of "treating" or "treatment"), arresting the development of the disease, disorder, symptom or condition as measured by clinical or sub-clinical parameters, ameliorating or causing regression of the disease, disorder, symptom or condition as measured by clinical or sub-clinical parameters, or reducing pain or discomfort for the mammal treated as measured by clinical and/or pharmacological parameters. "Treating" does not include preventing the onset of the disease or condition.

As used herein the term "muscular dystrophy" or "muscular dystrophies" refers to a group of hereditary muscle diseases that weakens the muscles that move the mammalian body. Muscular dystrophies are characterized by a genetic defect resulting in muscle weakness or loss of muscle tissue which progressively increases over time. By way of example only, diseases classified as muscular dystrophy include Duchenne, Becker, limb girdle, congenital, facioscapulohumeral, myotonic, oculopharyngeal, distal, Ulrich and Emery-Dreifuss.

The term "muscle degeneration" refers to a disease of the muscle characterized by a reduction in muscle mass or death of muscle cells. "Cell death" as used herein refers to the death of cells by both apoptotic and necrotic means.

The term "muscle cells" as used herein refers to any cell-type found in muscles. Examples of cell-types found within the muscles of mammals include myocytes, myoblasts, skeletal muscle cells, cardiac muscle cells, and smooth muscle cells. Methods of this invention exclude the treatment of cardiac muscle cells, for example, cardiomyocytes.

Oxidative stress represents an imbalance between the production and manifestation of reactive oxygen species and a biological system's ability to readily detoxify the reactive intermediates or to repair the resulting damage. Disturbances in the normal redox state of tissues can cause toxic effects through the production of peroxides and free radicals that damage all components of the cell, including proteins, lipids, and DNA. Some reactive oxidative species can even act as messengers through a phenomenon called redox signaling.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

A "pharmaceutically acceptable solvate or hydrate" of a compound of the invention means a solvate or hydrate complex that is pharmaceutically acceptable and that possesses the desired pharmacological activity of the parent compound, and includes, but is not limited to, complexes of a compound of the invention with one or more solvent or water molecules, or 1 to about 100, or 1 to about 10, or one to about 2, 3 or 4, solvent or water molecules.

"Alkyl" refers to monovalent saturated aliphatic hydrocarbyl groups having (unless specified as otherwise) from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl ($(CH_3)_2CH$—), n-butyl ($CH_3CH_2CH_2CH_2$—), isobutyl ($(CH_3)_2CHCH_2$—), sec-butyl ($(CH_3)(CH_3CH_2)CH$—), t-butyl ($(CH_3)_3C$—), n-pentyl ($CH_3CH_2CH_2CH_2CH_2$—), and neopentyl ($(CH_3)_3CCH_2$—). Lower alkyl refers, preferably, to $C_1$-$C_4$ alkyl.

"Alkylene" refers to branched or straight chain $C_1$-$C_{20}$ hydrocarbon, preferably having from 1 to 10 carbon atoms such as methylene, ethylene, propylene, isopropylene, n-butylene, pentylene, n-hexylene and the like.

"Aryl" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO3H, substituted sulfonyl, substituted sulfonyloxy, thioacyl, thiol, alkylthio, and substituted alkylthio, wherein said substituents are as defined herein.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems. In fused ring systems, one or more the rings can be cycloalkyl, aryl, or heteroaryl provided that the point of attachment is through a non-aromatic ring. In one embodiment, the nitrogen and/or sulfur atom(s) of the heterocyclic group are optionally oxidized to provide for the N-oxide, sulfinyl, or sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, and cyclooctyl.

"Cycloalkenyl" refers to non-aromatic cyclic alkyl groups of from 3 to 10 carbon atoms having single or multiple cyclic rings and having at least one >C=C< ring unsaturation and preferably from 1 to 2 sites of >C=C< ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thioxo, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO3H, substituted sulfonyl, substituted sulfonyloxy, thioacyl, thiol, alkylthio, and substituted alkylthio, wherein said substituents are as defined herein.

"Halo" or "halogen" refers to fluoro, chloro, bromo and iodo.

2. METHODS OF THE INVENTION

In one aspect, the invention provides a method of inhibiting the production of reactive oxygen species in a cell overproducing reactive oxygen species which method comprises contacting the cell with an effective amount of a monoamine oxidase inhibitor compound of Formula I:

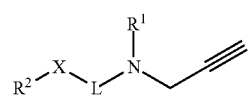

wherein $R^1$ is H or $C_1$-$C_6$ alkyl;

L is a covalent bond or $C_1$-$C_6$ straight chain or branched alkylene;

X is a covalent bond or O, S, or N;

$R^2$ is an aryl, heteroaryl, heterocycle, cycloalkyl, cycloalkenyl, each of which can optionally be substituted with 1-3 substituents selected from halogen or nitrogen; wherein the muscle cell is not a cardiomyocyte. In one embodiment, the cell overproducing the reactive oxygen species is a cell with the characteristics of muscle dystrophy.

In another aspect, the invention provides a method for preventing or treating muscle dystrophy wherein the etiology of said muscle dystrophy includes overproducing reactive oxygen species which method comprises administering a therapeutically effective amount of a compound of formula I to reduce or prevent the production of reactive oxygen species, thereby treating muscle dystrophy. Since compounds of the invention are useful for preventing the production of harmful reactive oxygen species (ROS) rather than scavenging already produced ROS, it is contemplated that compounds of this invention can be used to prevent muscle degeneration in mammals diagnosed with a disease classified as muscle dystrophy but not yet manifested in said mammal.

Muscular dystrophies are characterized by a genetic defect resulting in muscle weakness or loss of muscle tissue which progressively increases over time. Without being limited to any particular theory, it is contemplated that administration of MAO inhibitors reduces the production and accumulation of ROS. The consequence of such reduction and accumulation is a reduction in the degeneration of muscle that occurs in response to oxidative damage.

Methods of diagnosing muscle dystrophy or a disease classified as muscular dystrophy are well known in the art. By way of example, such methods include muscle biopsy to access necrosis and variation of muscle fiber size, elevated creatine phosphokinase levels, immunostaining analysis of dystrophin, a DNA blood test to test for abnormal protein dystrophin, and/or physical examination.

In one embodiment of the invention, the compounds of the invention are administered in an amount that inhibits a monoamine oxidase protein. In a related embodiment, the compounds of the invention are administered in an amount inhibits a monoamine oxidase-A protein, or alternatively in another embodiment, a monoamine oxidase-B protein. The level of inhibition of MAO proteins is easily determined by methods well known to those skilled in the art. For example, a MAO activity assay as detailed in Example 2 can be employed using muscle tissue biopsied from a patient.

Another indication of the efficacy of a compound and/or the inhibition of a MAO protein include the measurement of the reduced form of a myofibrillar protein, for example, tropomyosin, by immunoblots of muscle tissue as detailed in Example 7.

In one embodiment, the method includes administration of a compound of the formula Ia:

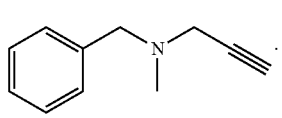

Ia

The compound of formula Ia is commonly known as pargyline and inhibits MAO-A and MAO-B protein activity.

In another embodiment, the compound administered in the methods described herein is a compound tabulated in Table 2 below:

TABLE 2

| Structure | Common Name | IUPAC name |
|---|---|---|
| 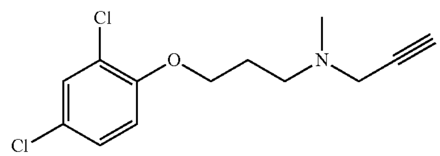 [SMILES: C#CCN(C)CCCOc1ccc(Cl)cc1Cl] | Clorgiline | N-[3-(2,4-dichlorophenoxy)propyl]-N-methyl-prop-2-yn-1-amine |
| 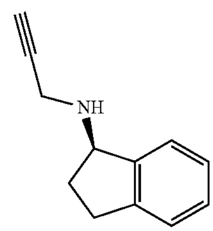 | Rasagiline | (R)-N-(prop-2-ynyl)-2,3-dihydro-1H-inden-1-amine |
| 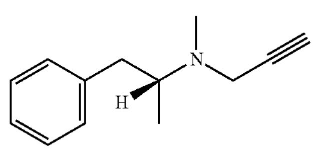 | Selegline | (R)-N-methyl-N-(1-phenylpropan-2-yl)prop-2-yn-1-amine |
| 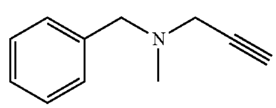 | Pargyline | N-Benzyl-N-methylprop-2-yn-1-amine |
| 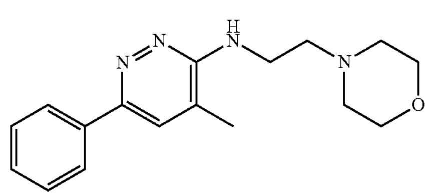 [SMILES: Cc1cc(-c2ccccc2)nnc1NCCN1CCOCC1] | Minaprine | 4-methyl-N-(2-morpholin-4-ylethyl)-6-phenylpyridazin-3-amine |
| 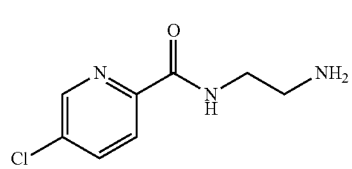 [SMILES: NCCNC(=O)c1ccc(Cl)cn1] | Lazabemide | N-(2-aminoethyl)-5-chloro-pyridine-2-carboxamide |

TABLE 2-continued

| Structure | Common Name | IUPAC name |
| --- | --- | --- |
| 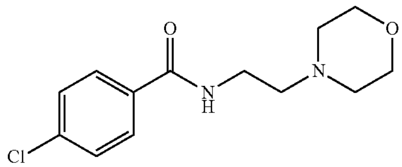 [SMILES: O=C(NCCN1CCOCC1)c1ccc(Cl)cc1] | Moclobemide | 4-chloro-N-(2-morpholin-4-ylethyl)benzamide |
| 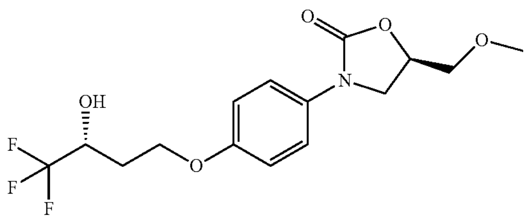 [SMILES: COC[C@H]1CN(c2ccc(OCC[C@@H](O)C(F)(F)F)cc2)C(=O)O1] | Befloxatone | (R)-5-(methoxymethyl)-3-(4-((R)-4,4,4-trifluoro-3-hydroxybutoxy)phenyl)-oxazolidin-2-one |
| 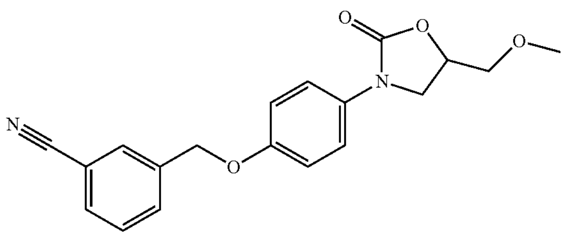 [SMILES: COCC1CN(c2ccc(OCc3cccc(C#N)c3)cc2)C(=O)O1] | Cimoxatone | 3-[[4-[5-(methoxymethyl)-2-oxo-oxazolidin-3-yl]phenoxy]methyl]benzonitrile |
| 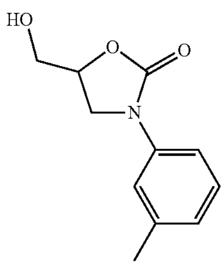 | Toloxatone | 5-(hydroxymethyl)-3-m-tolyloxazolidin-2-one |
| 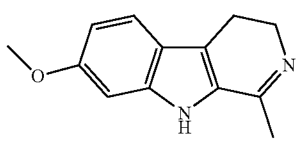 [SMILES: COc1ccc2c3c([nH]c2c1)C(C)=NCC3] | Harmaline | 7-methoxy-1-methyl-4,9-dihydro-3H-pyrido[3,4-b]indole |
| 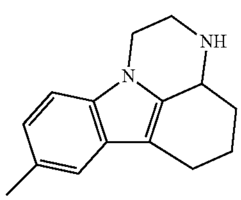 [SMILES: Cc1ccc2c(c1)c1c3n2CCNC3CCC1] | Pirlindole | 8-methyl-2,3,3a,4,5,6-hexahydro-1H-pyrazino[3,2,1-jk]carbazole |
| 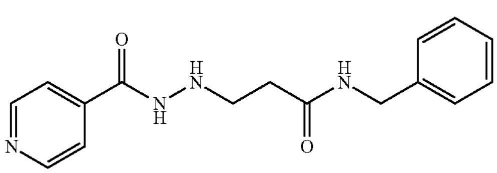 [SMILES: O=C(CCNNC(=O)c1ccncc1)NCc1ccccc1] | Nialamide | N-benzyl-3-(N'-(pyridine-4-carbonyl)hydrazino)propanamide |
| 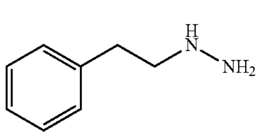 | Phenelzine | (±)-2-phenylethylhydrazine |

TABLE 2-continued

| Structure | Common Name | IUPAC name |
|---|---|---|
| 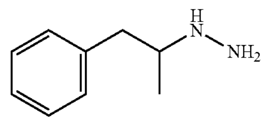 | Pheniprazine | (1-methyl-2-phenyl-ethyl)hydrazine |
| 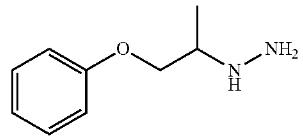 | Phenoxypropazine | (1-methyl-2-phenoxy-ethyl)hydrazine |
| 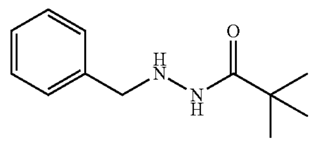 | Pivalylbenzhydrazine | N'-benzyl-2,2-dimethyl-propanehydrazide |
| 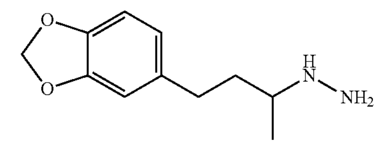 | Safrazine | [3-(1,3-benzodioxol-5-yl)-1-methyl-propyl]hydrazine |
| 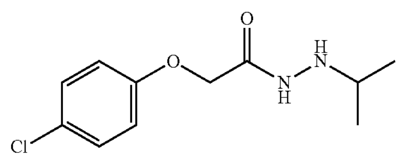 [SMILES: CC(C)NNC(=O)COc1ccc(Cl)cc1] | Iproclozide | 2-(4-chlorophenoxy)-N'-isopropyl-acetohydrazide |
| 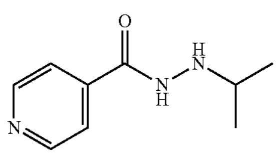 | Iproniazid | N'-isopropylisonicotinohydrazide |
| 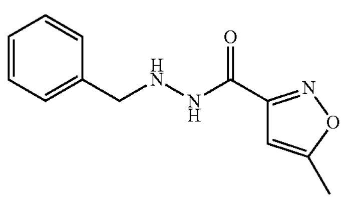 [SMILES: Cc1cc(C(=O)NNCc2ccccc2)no1] | Isocarboxazid | N'-benzyl-5-methylisoxazole-3-carbohydrazide |
| 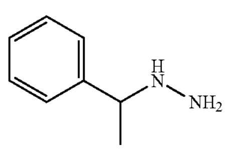 | Mebanazine | 1-phenylethylhydrazine |
| 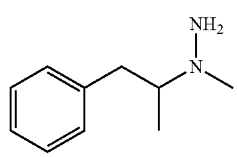 | Metfendrazine | 1-methyl-1-(1-methyl-2-phenyl-ethyl)hydrazine |
| 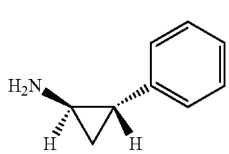 | Tranycypromine | (±)-trans-2-phenylcyclopropan-1-amine |

TABLE 2-continued

| Structure | Common Name | IUPAC name |
|---|---|---|
| 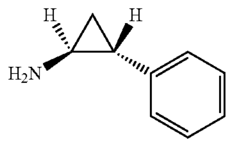 | Tranycypromine | (1R*,2S*)-2-phenylcyclopropan-1-amine |
| 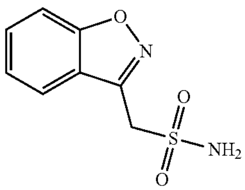 [SMILES: NS(=O)(=O)Cc1noc2ccccc12] | Zonisamide | benzo[d]isoxazol-3-ylmethanesulfonamide |
| 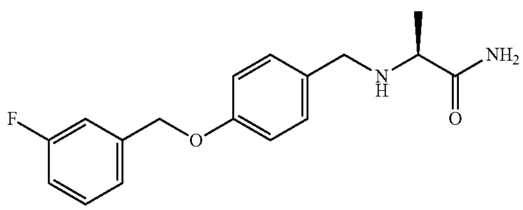 [SMILES: C[C@H](NCc1ccc(OCc2cccc(F)c2)cc1)C(N)=O] | Safinamide | N²-{4-[(3-fluorobenzyl)oxy]benzyl}-L-alaninamide |

In yet another aspect, the compound administered in the methods described herein is a compound selected from the group consisting of:

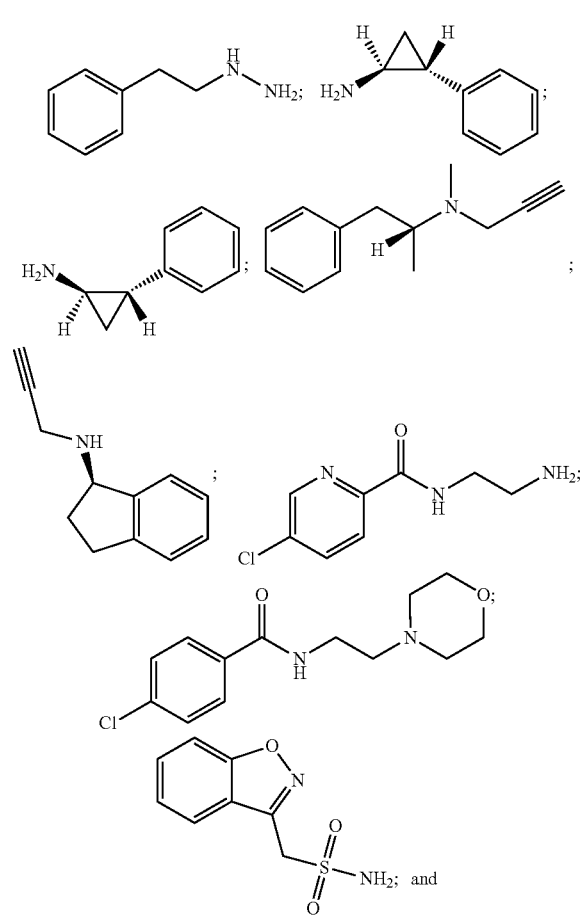

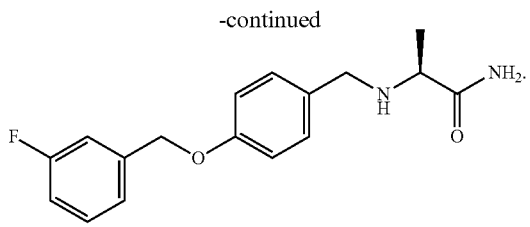

Others aspects of the invention relate to a compound of the Formula I:

I wherein $R^1$ is H or $C_1$-$C_6$ alkyl;
L is a covalent bond or $C_1$-$C_6$ straight chain or branched alkylene;
X is a covalent bond or O, S, or N;
$R^2$ is an aryl, heteroaryl, heterocycle, cycloalkyl, cycloalkenyl, each of which can optionally be substituted with 1-3 substituents selected from halogen or nitrogen.

Another aspect of the invention relates to a pharmaceutical composition comprising a therapeutically effective amount of the compound of Formula I and at least one pharmaceutical excipient.

Pharmaceutical compositions can be formulated for different routes of administration such as oral, intravenous, intraarterial, pulmonary, rectal, nasal, vaginal, lingual, intramuscular, intraperitoneal, intracutaneous, transdermal and subcutaneous routes. Other dosage forms include tablets, capsules, pills, powders, aerosols, suppositories, parenterals, and oral liquids, including suspensions, solutions and emulsions. Sustained release dosage forms may also be used, for example, in a transdermal patch form. All dosage forms may be prepared using methods that are standard in the art (see e.g., Remington's Pharmaceutical Sciences, 16th ed., A. Oslo editor, Easton Pa. 1980).

The compositions are comprised of in general, a compound of this invention with at least one pharmaceutically acceptable excipient. Acceptable excipients are non-toxic, aid administration, and do not adversely affect the therapeutic benefit of the compound of this invention. Such excipients may be any solid, liquid, semi-solid or, in the case of an aerosol composition, gaseous excipient that is generally available to one of skill in the art. Pharmaceutical compositions in accordance with the invention are prepared by conventional means using methods known in the art.

The compositions disclosed herein may be used in conjunction with any of the vehicles and excipients commonly employed in pharmaceutical preparations, e.g., talc, gum arabic, lactose, starch, magnesium stearate, cocoa butter, aqueous or non-aqueous solvents, oils, paraffin derivatives, glycols, etc. Coloring and flavoring agents may also be added to preparations, particularly to those for oral administration. Solutions can be prepared using water or physiologically compatible organic solvents such as ethanol, 1,2-propylene glycol, polyglycols, dimethylsulfoxide, fatty alcohols, triglycerides, partial esters of glycerine and the like.

Solid pharmaceutical excipients include starch, cellulose, hydroxypropyl cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc.

The concentration of the excipient is one that can readily be determined to be effective by those skilled in the art, and can vary depending on the particular excipient used.

Compounds of this invention may be used alone or in combination with other compounds. When administered with another agent, the co-administration can be in any manner in which the pharmacological effects of both are manifest in the patient at the same time. Thus, co-administration does not require that a single pharmaceutical composition, the same dosage form, or even the same route of administration be used for administration of both the compound of this invention and the other agent or that the two agents be administered at precisely the same time. However, co-administration will be accomplished most conveniently by the same dosage form and the same route of administration, at substantially the same time. Obviously, such administration most advantageously proceeds by delivering both active ingredients simultaneously in a novel pharmaceutical composition in accordance with the present invention.

In some embodiments, a compound of this invention can be used as an adjunct to conventional drug therapy or other therapeutic modalities traditionally used to treat muscle dystrophies. Traditional therapies for muscle dystrophies include, for example, physical therapy, respiratory therapy, speech therapy, orthopedic appliances used for support, and corrective orthopedic surgery. Drug therapy includes corticosteroids to slow muscle degeneration, anticonvulsants to control seizures and some muscle activity, immunosuppressants to delay some damage to dying muscle cells, and antibiotics to fight respiratory infections. Some patients may benefit from occupational therapy and assistive technology. Some patients may need assisted ventilation to treat respiratory muscle weakness and a pacemaker for cardiac abnormalities.

EXAMPLES

The practice of the present invention employs, unless otherwise indicated, conventional techniques of molecular biology (including recombinant techniques), microbiology, cell biology, biochemistry, pharmacology, immunology, and chemistry, which are well within the skill of on of art. Such techniques are explained fully in the literature for example in the following publications. See, e.g., Sambrook and Russell eds. MOLECULAR CLONING: A LABORATORY MANUAL, 3rd edition (2001); the series CURRENT PROTOCOLS IN MOLECULAR BIOLOGY (F. M. Ausubel et al. eds. (2007)); the series METHODS IN ENZYMOLOGY (Academic Press, Inc., N.Y.); PCR 1: A PRACTICAL APPROACH (M. MacPherson et al. IRL Press at Oxford University Press (1991)); CULTURE OF ANIMAL CELLS: A MANUAL OF BASIC TECHNIQUE (R.I. Freshney 5th edition (2005)); and GOOMAN AND GILLMAN'S THE PHARMACOLOGICAL BASIS OF THERAPEUTICS (Brunton et al. McGraw Hill Publishing (2005)).

Example 1

Mice and Pargyline Treatment In Vivo

Col6a1$^{+/-}$ mice were backcrossed in the inbred C57BL/6J strain for eight generations as described (Irwin, W. A., et al., (2003) Nat. Genet., 35, 367-371), and data were obtained by comparing Col6a1$^{-/-}$ mice with their wild-type littermates. Wild-type C57BL/10 mice and mdx (in the C57BL/10 background) were obtained from Charles River and Jackson Laboratories, respectively. Pargyline (50 mg/kg/days) or vehicle (phosphate-buffered saline, PBS) were administered by daily intraperitoneal (i.p.) injection for 7 days in 6-month-old Col6a1$^{-/-}$ and C57BL/6J male mice or 5-week-old mdx and C57BL/10 male mice. During the treatment, mice were placed in separate cages with a running wheel. At the end of the treatment, mice were sacrificed and muscles were removed and stored in liquid nitrogen until use.

Example 2

MAO Activity Assay

Muscle cryosections were suspended in PBS and centrifuged at 500 g for 10 min at 4° C. The supernatant was centrifuged at 8000×g for 10 min at 4° C. and the resulting pellet was resuspended in PBS and stored on ice until use. Protein concentration was determined by the Bradford assay (Bio-Rad). MAO activity assay was based on the detection of hydrogen peroxide generated during substrate catabolism in a horseradish peroxidase (HRP) coupled reaction using 10-acetyl-3,7-dihydroxyphenoxazine (Amplex Red reagent, Molecular Probes). The mitochondrial protein extracts (40 mg) were incubated in PBS with 10 mM Amplex Red and 15 mg/ml HRP. The reaction was started by the addition of 250 mM tyramine, a MAO-A and MAO-B substrate. The fluorescence intensity was recorded at 37° C. using a Perkin Elmer LS-50B fluorimeter at the 544/590 nm excitation/emission wavelengths. Parallel samples were run in the absence of a substrate to take into account the increase in fluorescence not due to MAO activity.

Example 3

DHE Staining for ROS Detection

DHE is oxidized by ROS, forming ethidium bromide, which emits red fluorescence when intercalates with DNA (Benov, L., et al., (1998) Free Radic. Biol. Med., 25, 826-831). Skeletal muscle cryosections (10 µm thick) were incubated with 5 mM DHE (Sigma) in PBS at 37° C. for 30 min in humid atmosphere and in the dark, washed twice with PBS, mounted and visualized with an Olympus IMT-2 inverted microscope, equipped with a xenon lamp and a 12-bit digital cooled CCD camera (Micromax, Princeton Instruments) as previously described (Petronilli, V., et al., (1999) Biophys. J., 76, 725-734). For the detection of the fluorescence, 568±25 nm excitation and 585 nm long-pass emission filter settings were used. Data were acquired and analyzed using Metamorph software (Universal Imaging).

Example 4

Protein Extraction and Immunoelectrophoresis

Protein extracts were prepared as described (Canton, M., et al., (2006) Eur. Heart J., 27, 875-881). Immunoblotting were stained with the following antibodies: anti-Tm CH1 clone (Sigma), anti-MAO-B D-16 and anti-MAO-A H-70 clone (Santa Cruz). In anti-Tm immunoblots, the high-molecular-mass peptides were attributed to disulfide cross-bridges (DCB) formation by comparing electrophoreses carried out in the absence or in the presence of β-mercaptoethanol as described (Canton, M., et al., (2006) Eur. Heart J., 27, 875-881). Quantitation of Tm oxidation was performed by densitometric analysis of the bands obtained under non-reducing conditions (ImageJ software). DCB density was normalized to the actin density in Red Ponceau to take differences in sample loading into account. Data were expressed as percentage of DCB relative to vehicle-treated wild-type mice.

Example 5

Pathological Markers

Cross-sections (7 µm thick) were prepared and processed for hematoxylin and eosin (H&E) staining For the morphometric analysis of myofiber cross sectional areas (CSAs), we counted approximately 2000 fibers per mouse for each muscle type by means of ImageJ software. At least three sections from each muscle were analyzed. TUNEL (terminal deoxynucleotidyl transferase-mediated dUTP nick end-labeling) was performed on paraffin-embedded sections (7 µm thick) using the ApopTag in situ apoptosis detection kit (Chemicon). Samples were stained with peroxidase diaminobenzidine to detect TUNEL-positive nuclei and counterstained with Hoechst 33258 to identify all nuclei, as described previously (Irwin, W. A., et al., (2003) Nat. Genet, 35, 367-371). The total number of nuclei and number of TUNEL-positive nuclei were determined in randomly selected fibers using a Zeiss Axioplan microscope equipped with a Leica DC 500 camera. Membrane permeability of skeletal muscle was directly visualized by immunohistochemical staining with IgG (Weller, B., et al., (1990) J. Neurol. Sci., 100, 9-13 and Blaauw, B., et al., (2008) Hum. Mol. Genet., 17, 3686-3696). Cryosections (10 µm thick) were incubated with anti-mouse fluorescein isothiocyanate-conjugated IgG, washed twice with PBS, mounted and visualized with an Olympus IMT-2 inverted microscope as previously described (Petronffli, V., et al., (1999) Biophys. J., 76, 725-734) using excitation/emission cubes of 488/525±25 nm bandpass. Evans blue dye staining of muscles in vivo was performed by i.p. injection with 0.2 ml Evans blue (10 mg/ml in PBS; Sigma). Mice were sacrificed after 16-18 h and diaphragms were fixed with 4% paraformaldehyde overnight at 4° C. After fixation, the samples were observed by means of light microscopy.

Example 6

Muscle Functional Assessment

Single myofibers were isolated from Col6a1$^{-/-}$ gastrocnemius muscle, chemically skinned as described (Rossi, R., et aL, (2001) Am. J. Physiol. Cell Physiol., 281, C585-C594.) and tension was measured during maximal isometric activation (pCa=4.5, T=20° C., initial sarcomere length=2.75 µm). Force measurements were performed in the left and/or right gastrocnemius muscle of anesthetized mice by electrical stimulation through the sciatic nerve, as described previously (Blaauw, B., et al., (2008) Hum. Mol. Genet., 17, 3686-3696). Voluntary exercise was evaluated by placing a wheel in the cage. Before the treatment, mice were placed in separate cages with wheel to acclimatize, then the average distance covered by each mouse in 24 h during the treatment was measured using an automatic counter.

Example 7

Myofibrillar Protein Oxidation in Col6a1$^{-/-}$ Mice and Effects of MAO Inhibition Two murine models of MD were considered in this study: Col6a1$^{-/-}$ mice, which lack collagen VI due to null mutation of the gene coding for the a1(VI) subunit (Bonaldo, P., et al., (1998) Hum. Mol. Genet., 7, 2135-2140), and mdx mice, which lack dystrophin (Sicinski, P., et al., (1989) Science, 244, 1578-1580). The activity of MAO in skeletal muscle was first investigated, and it was found that it was significantly increased in 6-month-old Col6a1$^{-/-}$ mice when compared with wild-type littermates (FIG. 1A). The increased MAO activity was associated with an increase in MAO-A protein levels in Col6a1$^{-/-}$ muscle (FIG. 1B). To assess the role of MAO-dependent ROS accumulation, Col6a1$^{-/-}$ mice were randomized into groups receiving i.p. treatment with pargyline (50 mg/kg/day), an MAO-A and MAO-B inhibitor, or vehicle for 1 week. MAO activity was abolished after the treatment (FIG. 1A). Next, we quantified ROS production in 6-month-old Col6a1$^{-/-}$ mice. When compared with age-matched wildtype mice, muscles of Col6a1$^{-/-}$ mice showed an increased accumulation of ROS, as revealed by increased dihydroethidium (DHE) fluorescence in diaphragm and gastrocnemius (FIG. 1C). Importantly, the abnormal production of ROS in Col6a1$^{-/-}$ muscles was significantly decreased upon pargyline treatment (FIGS. 1C and D).

Figure 2:
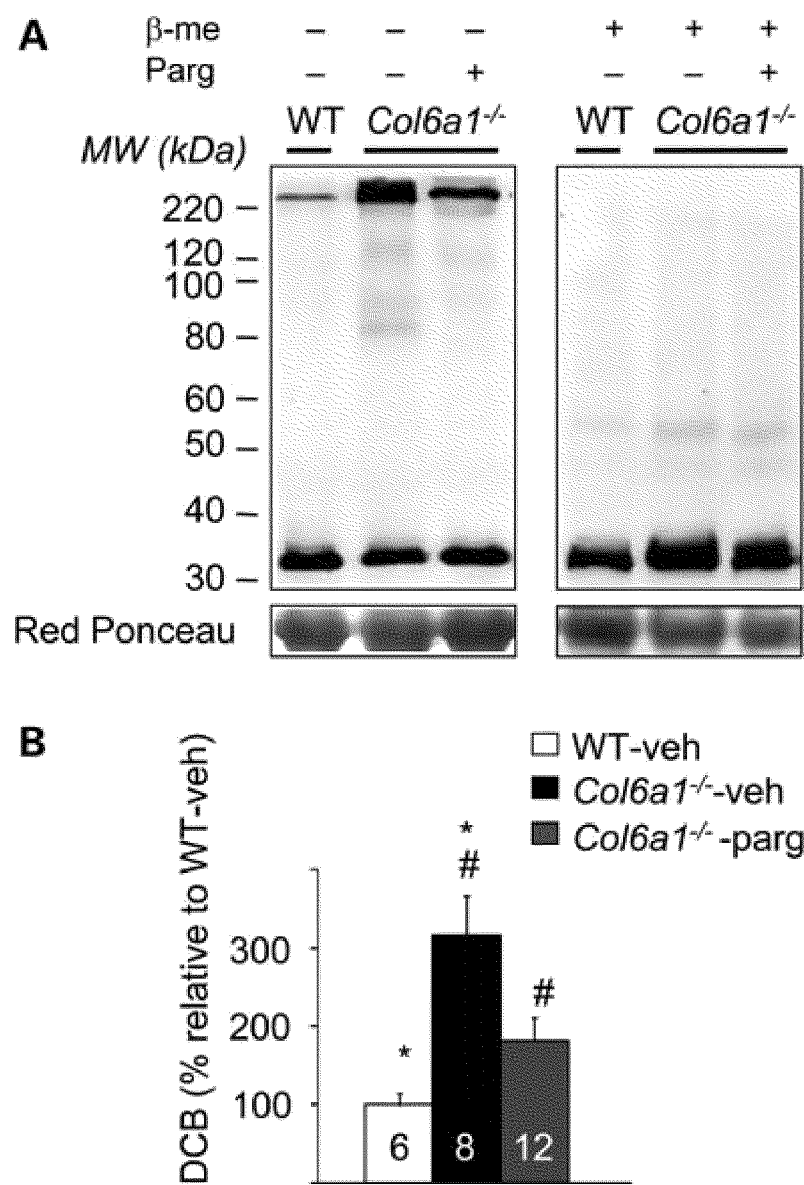
FIG. 2 demonstrates that MAO inhibition reduces Tm oxidation in Col6a1$^{-/-}$ mice.

Then, it was investigated whether MAO-dependent ROS accumulation caused oxidative modifications of myofibrillar proteins, as probed by Tm (tropomyosin) oxidation. Indeed, it was previously demonstrated that, among myofibrillar proteins, Tm is particularly susceptible to oxidative stress (Canton, M., et al., (2006) Eur. Heart J., 27, 875-881). Immunoblots with anti-Tm displayed additional high molecular mass bands in Col6a1$^{-/-}$ diaphragm, which is the most affected muscle in this murine model (FIG. 2A). The appearance of these bands, which were much fainter in samples obtained from wild-type littermates, reflected disulfide cross-bridges (DCBs) formation because they were visible only under non-reducing electrophoresis. The band at 82 kDa was attributed to a dimer of Tm, while the bands with an apparent molecular mass >220 kDa could reflect high molecular mass complexes among several monomers of Tm or between Tm and other proteins. It is worth pointing out that skeletal Tm contains the a well as the β-isoform. At variance from the presence of a single cysteine in the α-isoform, β-Tm contains two Cys residues that might result in the covalent aggregation of more than two proteins by means of DCB formation. Indeed, mass spectrometric analysis performed on the high molecular mass Tm complexes identified the myosin heavy chain (Data not shown). DCB content was 3.2±0.4-fold higher in Col6a1$^{-/-}$ when compared with wild-type muscles and was significantly reduced by pargyline treatment (FIG. 2B).

Example 8

MAO Inhibition Ameliorates Muscle Apoptotic Phenotype of Col6a1$^{-/-}$ Mice

Figure 3:
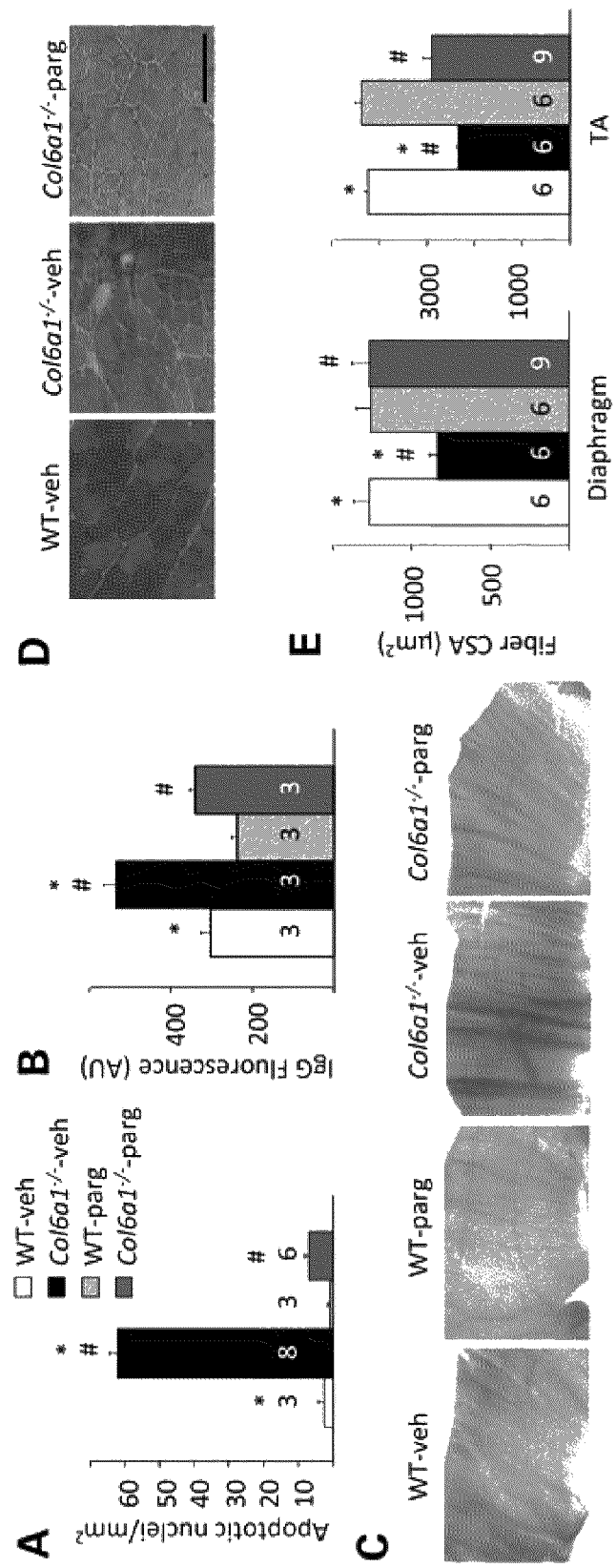
FIG. 3 demonstrates that MAO inhibition rescues histological alterations and prevents muscle apoptosis in Col6a1$^{-/-}$ mice.

Contractile impairment and high apoptosis rate are two specific features of skeletal muscles of Col6a1$^{-/-}$ mice (Irwin, W. A., et al., (2003) Nat. Genet., 35, 367-371). It was therefore investigated whether pargyline treatment was able to improve cell survival and to counteract the apoptotic phenotype observed in Col6a1$^{-/-}$ mice. Occurrence of apoptosis was evaluated by TUNEL. The number of TUNEL-positive nuclei was higher in Col6a1$^{-/-}$ mice when compared with wild-type littermates (62.4±2.3 versus 2.7±1.2 nuclei/mm$^2$), and pargyline treatment reduced the occurrence of TUNEL-positive nuclei to a level (6.9±1) that was not significantly different from that observed in wild-type mice (FIG. 3A). Direct evidence of a protective effect of MAO inhibition on muscle damage was provided by immunohistochemical staining of skeletal muscle with IgG antibody. In fact, the circulating IgG can enter into the myfibers of dystrophic mice due to altered sarcolemma integrity, thus allowing their detection by FITC-conjugated anti-mouse IgG (18,19). Damaged fibers, positive to the immunohistochemical staining for IgG, were present in Col6a1$^{-/-}$ diaphragm and their number was significantly decreased by pargyline treatment (FIG. 3B). Additional evidence of muscle damage and protection by MAO inhibition was provided by vital staining with Evans blue. Supporting the finding obtained by permeability to IgG, several damaged myofibers stained by Evans blue were found in Col6a1$^{-/-}$ but not in wild-type diaphragm, and this alteration was largely reduced in the diaphragm of Col6a1$^{-/-}$ mice treated with pargyline (FIG. 3C). Morphometric analysis of myofiber cross-sectional areas (CSAs) in tibialis anterior and diaphragm showed that Col6a1$^{-/-}$ muscles contained myofibers of different sizes, with a prevalence of small fibers. This pathological sign was markedly reduced in pargyline-treated Col6a1$^{-/-}$ muscles, which showed more uniform fiber size, similarly to wild-type mice (FIGS. 3D and E).

Example 9

MAO Inhibition Ameliorates Muscle Dysfunction in Col6a1$^{-/-}$ Mice

Figure 4:
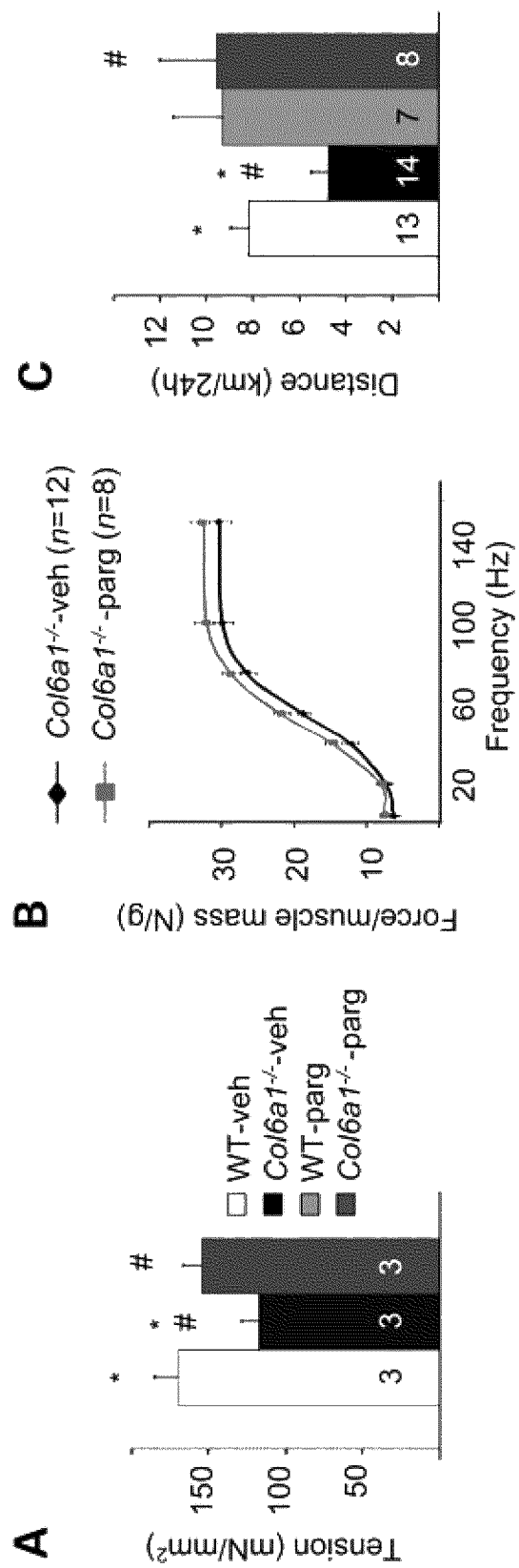
FIG. 4 shows that MAO inhibition ameliorates muscle alterations in Col6a1$^{-/-}$ mice.

Biochemical and histological analyses were paralleled by functional assessment of the contractile performance of muscles in vivo and isolated muscle fibers in vitro. Single-skinned muscle fibers dissected from gastrocnemius muscle were maximally calcium-activated at optimal sarcomere length. Col6a1$^{-/-}$ fibers developed lower isometric tension than wild-type fibers, as previously reported (Irwin, W. A., et al., (2003) Nat. Genet., 35, 367-371; Blaauw, B., et al., (2010) J. Appl. Physiol., 108, 105-111). The contractile impairment disappeared in the fibers of pargyline-treated Col6a1$^{-/-}$ mice (FIG. 4A). This in vitro evidence was further supported by in vivo findings, as pargyline treatment significantly increased the normalized force of gastrocnemius muscle of Col6a1$^{-/-}$ mice (FIG. 4B). It was tested whether treatment with pargyline could improve the voluntary exercise performance of Col6a1$^{-/-}$ mice, tested by means of a running wheel. After acclimatizing mice for 1 week to a wheel placed in their cage, the daily average distance was measured. The pargyline-treated Col6a1$^{-/-}$ mice showed a significant improvement in the exercise performance compared with untreated mice (FIG. 4C).

Example 10

MAO Inhibition Rescues Dystrophic Phenotype in mdx Mice

The findings obtained in Col6a1$^{-/-}$ mice prompted the investigation of whether ROS generated by MAO might play a role also in mdx mice, where ROS accumulation has been previously demonstrated (Tidball, J. G. and Wehling-Henricks, M. (2007) J. Appl. Physiol., 102, 1677-1686 and Disatnik, M. H., et al., (1998) J. Neurol. Sci., 161, 77-84). Interestingly, MAO activity increased in the gastrocnemius muscle of mdx mice along with an increase in MAO-A protein levels (Data not shown), in accordance with what was observed in Col6a1$^{-/-}$ mice. Gastrocnemius and quadriceps of 5-week-old mdx mice displayed a significant increase in both ROS formation and Tm oxidation (Table 3 and FIG. 5A).

TABLE 3

Pargyline treatment reduces MAO-dependent ROS formation in mdx mice.

|  | Gastrocnemius | Quadriceps |
| --- | --- | --- |
| WT-veh mice (n = 8) | 100.0 ± 8.4 | 100.0 ± 8.3 |
| mdx-veh mice (n = 8) | 127.8 ± 9.0* | 119.3 ± 1.3* |
| WT-parg mice (n = 8) | 102.8 ± 2.8 | 96.9 ± 6.2 |
| mdx-parg mice (n = 8) | 105.6 ± 2.2# | 102.9 ± 1.5# |

Figure 5:
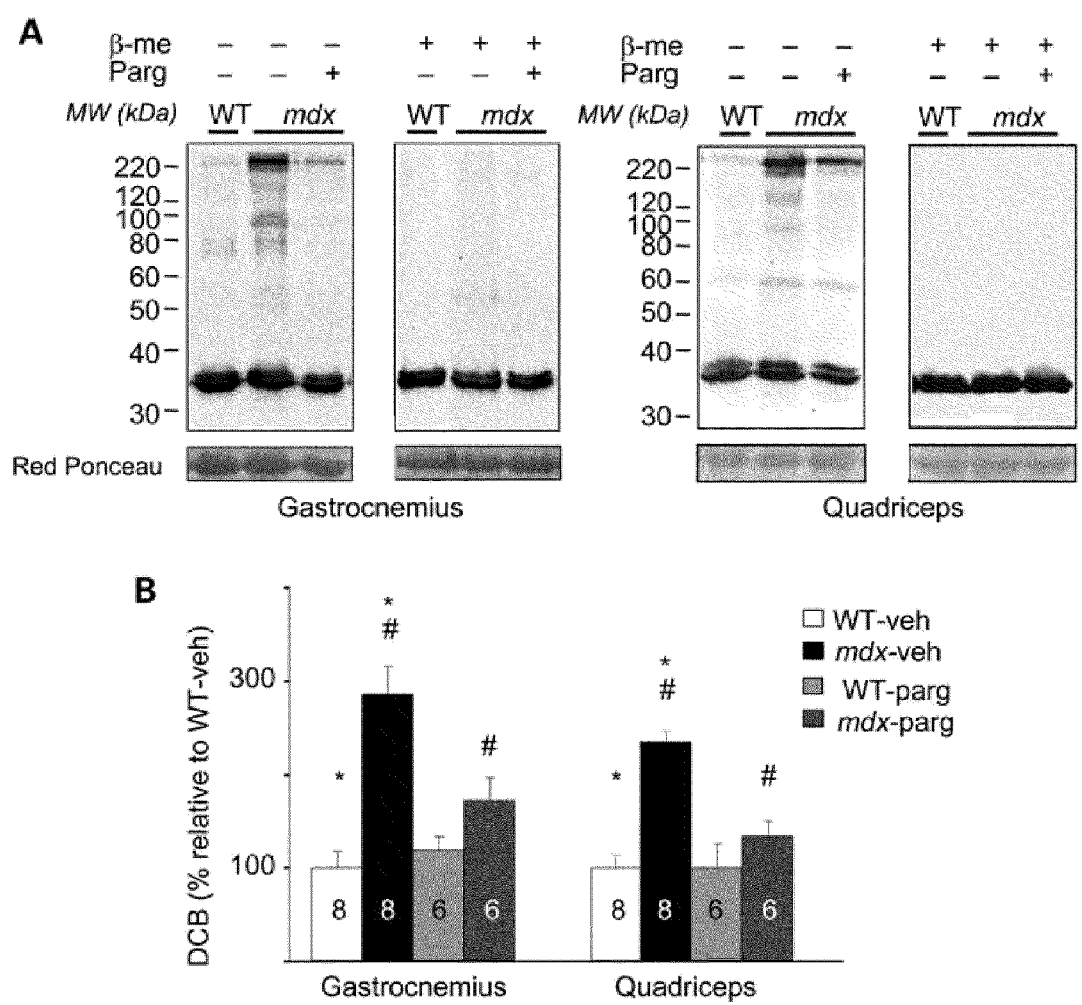
FIG. 5 depicts that Pargyline treatment reduces Tm oxidation in mdx mice.
Figure 6:
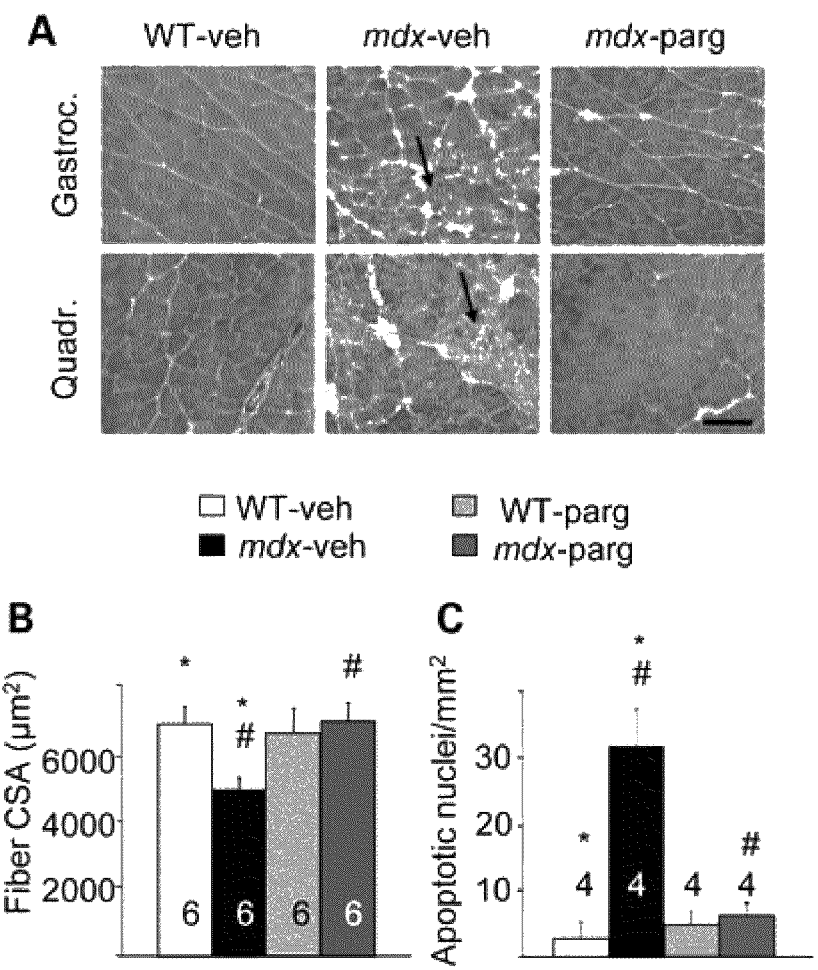
FIG. 6 demonstrates that Pargyline treatment ameliorates dystrophic pathology in mdx mice.

In fact, DCB increased by 2.84±0.31 and 2.34±0.28 folds in gastrocnemius and quadriceps muscle, respectively. Importantly, these oxidative modifications were significantly decreased after i.p. treatment with pargyline for 1 week (FIG. 5B). Morphometric analysis of myofiber CSAs in gastrocnemius muscle confirmed that mdx contained myofibers of different sizes, with a significant incidence of small fibers, while pargyline normalized the fiber area distribution (FIGS. 6A and B). In addition, pargyline was able to reduce tissue inflammation occurring in mdx skeletal muscles (FIG. 6A). The occurrence of apoptosis was markedly increased in mdx mice, yet pargyline treatment led to a significantly lower incidence in the number of TUNEL-positive nuclei of mdx mice (FIG. 6C). Taken together, these results indicate that also in mdx mice ROS generated by MAO are relevant to the dystrophic mechanism and that MAO inhibition protects dystrophic skeletal muscle by reducing myofiber degeneration and ROS production.

Example 11

The Increased Susceptibility to Oxidative Stress of COL6A1$^{-/-}$ Myoblasts is Reduced by MAO Inhibition The in vitro treatment of treatment of myoblasts can be predictive of the treatment of MD (Muscular dystrophy) patients or dystrophic mice. Indeed, the in vitro protective effect of Cyclosporin A on mitochondrial dysfunction observed in myoblasts of MD patients was paralleled by the efficacy of this drug on MD patients. See for e.g. Angelin, A., et al., (2007) Proc. Natl. Acad. Sci. U.S.A 104, no. 3(2007): 991-96 and Merlini, L., et al (2008) Proc. Natl. Acad. Sci. U.S.A 105, no. 13(2008):5225-29 each of which is herein incorporated by reference.

Figure 7:
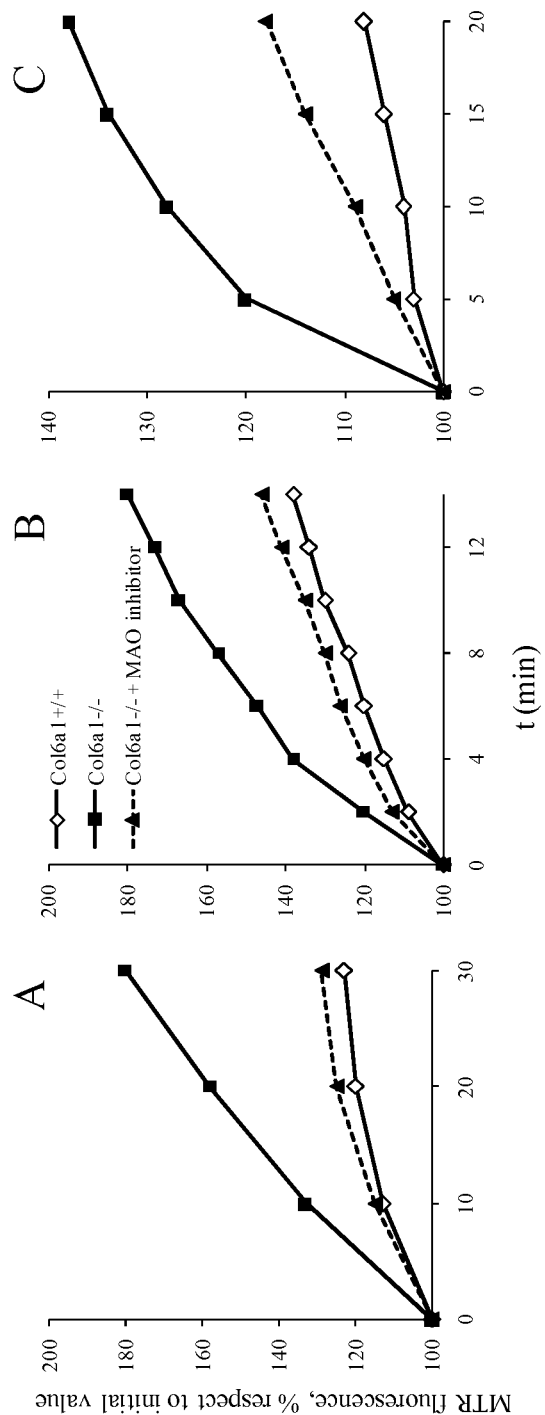
FIG. 7 demonstrates that the increased susceptibility to oxidative stress of Col6a1$^{-/-}$ myoblasts is reduced by MAO inhibition. Myoblasts obtained from the diaphragm of Col6a1$^{-/-}$ and Col6a1$^{+/+}$ mice were loaded with Mitotracker Red (MTR, 20 nM) to assess mitochondrial ROS production. After the first acquisition (with a fluorescence microscope), different inducers of oxidative stress (A: 100 uM $H_2O_2$, B: 5 uM arachidonic acid, C: 0.2 uM antimycin) were added and frames were collected at different intervals in the absence (filled square) and in the presence (filled triangles) of a MAO inhibitor (100 uM pargyline).

In addition, Applicants have demonstrated this relationship also in mice. The extent of ROS accumulation in myoblasts obtained from diaphragm of Col6a1$^{-/-}$ and Col6a1$^{+/+}$ mice was assessed. Myoblasts from Col6a1$^{-/-}$ mice, compared to their wild-type littermates, displayed an increased ROS production upon induction of oxidative stress (FIG. 7). As myoblasts from dystrophic mice showed an increased susceptibility to oxidative stress, Applicants investigated the contribution of MAOs. Remarkably, MAO inhibition reduced the presence of ROS in Col6a1$^{-/-}$ myoblasts underlying the relevance of ROS production due to MAO activity.

These results were paralleled by the studies on human myoblasts of patients.

Throughout this disclosure, various publications, patents and/or published patent specifications are referenced by an identifying citation. The disclosures of these publications, patents and published patent specifications are hereby incorporated by reference into the present disclosure to more fully describe the state of the art to which this invention pertains.

What is claimed is:

1. A method of inhibiting the production of reactive oxygen species in a muscle cell which method comprises contacting the cell with an effective amount of a monoamine oxidase inhibitor compound of Formula I:

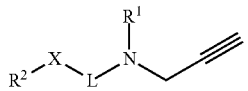

wherein $R^1$ is H or $C_1$-$C_6$ alkyl;
L is a covalent bond or $C_1$-$C_6$ straight chain or branched alkylene;
X is a covalent bond or O, S, or N;
$R^2$ is an aryl, heteroaryl, heterocycle, cycloalkyl, cycloalkenyl, each of which can optionally be substituted with 1-3 substituents selected from halogen or nitrogen; and
wherein the muscle cell is not a cardiomyocyte.

2. A method for treating muscular dystrophy in a patient which method comprises administering a therapeutically effective amount of a compound of formula I to reduce or prevent the production of reactive oxygen species, thereby treating muscle dystrophy:

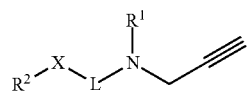

wherein $R^1$ is H or $C_1$-$C_6$ alkyl;
L is a covalent bond or $C_1$-$C_6$ straight chain or branched alkylene;
X is a covalent bond or O, S, or N;
$R^2$ is an aryl, heteroaryl, heterocycle, cycloalkyl, cycloalkenyl, each of which can optionally be substituted with 1-3 substituents selected from halogen or nitrogen.

3. The method of claim 1 wherein the compound is administered in an amount that inhibits a monoamine oxidase protein.

4. The method of claim 3 wherein the compound is administered in an amount that inhibits monoamine oxidase-A.

5. The method of claim 3 wherein the monoamine oxidase inhibitor is administered in an amount that inhibits monoamine oxidase-B.

6. The method of claim 1 wherein the compound is a compound of formula Ia:

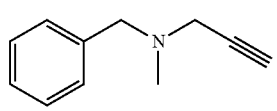

or a pharmaceutically acceptable salt thereof.

7. The method of claim 1 wherein the administration is in vivo to a mammal.

8. The method of claim 1 wherein the administration is in vitro.

* * * * *